(12) United States Patent
Fischer

(10) Patent No.: US 7,534,264 B2
(45) Date of Patent: May 19, 2009

(54) DELIVERY SYSTEM FOR BONE GROWTH PROMOTING MATERIAL

(75) Inventor: Dan E. Fischer, Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 594 days.

(21) Appl. No.: 10/766,503

(22) Filed: Jan. 28, 2004

(65) Prior Publication Data
US 2005/0163820 A1    Jul. 28, 2005

(51) Int. Cl.
*A61F 2/28*    (2006.01)

(52) U.S. Cl. .................... 623/16.11; 424/549

(58) Field of Classification Search ............... None
See application file for complete search history.

(56) References Cited

U.S. PATENT DOCUMENTS

| | | | |
|---|---|---|---|
| 2,423,707 A * | 7/1947 | Kenyon et al. ......... 139/426 R |
| 4,578,055 A | 3/1986 | Fischer ................... 604/2 |
| 4,728,570 A * | 3/1988 | Ashman et al. ............ 428/327 |
| 4,755,184 A * | 7/1988 | Silverberg ............... 623/23.56 |
| 4,863,472 A * | 9/1989 | Tormala et al. ........... 623/23.58 |
| 5,098,299 A | 3/1992 | Fischer .................. 433/215 |
| 5,292,253 A * | 3/1994 | Levy .................... 433/215 |
| 5,534,562 A | 7/1996 | Jensen et al. ............. 523/118 |
| 5,620,702 A | 4/1997 | Podell et al. ............. 424/448 |
| 5,635,162 A | 6/1997 | Fischer .................. 424/49 |
| 5,707,962 A * | 1/1998 | Chen et al. ............... 514/12 |
| 5,787,901 A | 8/1998 | Wilson .................. 128/898 |
| 5,837,258 A | 11/1998 | Grotendorst ............. 424/198.1 |
| 5,958,441 A | 9/1999 | Oppermann et al. ....... 424/423 |
| 5,985,315 A | 11/1999 | Patat et al. ............. 424/443 |
| 6,180,606 B1 | 1/2001 | Chen et al. ............... 514/12 |
| 6,287,341 B1 | 9/2001 | Lee et al. .............. 623/16.11 |
| 6,297,213 B1 | 10/2001 | Oppermann et al. ......... 514/12 |
| 6,306,424 B1 * | 10/2001 | Vyakarnam et al. ......... 424/426 |
| 6,326,018 B1 | 12/2001 | Gertzman et al. .......... 424/423 |
| 6,372,257 B1 | 4/2002 | Marchosky ............... 424/488 |
| 6,440,427 B1 | 8/2002 | Wadstrom ................ 424/400 |
| 6,458,162 B1 | 10/2002 | Koblish et al. ........... 623/23.51 |
| 6,565,606 B1 | 5/2003 | Bruce et al. ............. 623/23.63 |
| 6,565,884 B2 | 5/2003 | Nimni .................... 424/484 |
| 6,576,249 B1 | 6/2003 | Gendler et al. ........... 424/423 |
| 6,599,517 B1 | 7/2003 | Ljusberg-Wahren et al. 424/423 |
| 6,652,840 B1 | 11/2003 | Prevendar ................ 424/49 |
| 2003/0009147 A1 | 1/2003 | Bonutti ................. 604/500 |
| 2003/0026770 A1 | 2/2003 | Szymaitis ................ 424/50 |
| 2003/0135214 A1 | 7/2003 | Fetto et al. ............. 606/72 |
| 2003/0147860 A1 | 8/2003 | Marchosky .............. 424/93.7 |
| 2003/0166274 A1 | 9/2003 | Hewitt et al. ............ 435/366 |

FOREIGN PATENT DOCUMENTS

WO    WO9639203    12/1996

OTHER PUBLICATIONS

Cook, S.D., "Enhanced bone ingrowth and fixation strength with hydroxyapatite-coated porous implants", Database: PMID, Accession No. 10171176, Semin Arthroplasty, Oct. 1991—Abstract.
Damien, CJ, "Effect of demineralized bone matrix on bone growth within a porous HA material: a histologic and histometric study", Database: PMID, Accession No. 9309501, J. Biometer Appl., Jun. 1995—Abstract.
Cook, S.D., "The effect of demineralized bone matrix gel on bone ingrowth and fixation of porous implants", J. Database: PMID, Accession No. 12066267, J Arthroplasty, Jun. 2002—Abstract.
Chiroff, R. T., "Tissue ingrowth of Replamineform implants", J. Biomed Mater Res. Jul. 1975, http://www.sodbrenne-welt.de/science/1975/1975_1176509.xxl?ok.
University of Oxford, Project No. 542 "Bone Bonding Spheres", http://www.isis-innovation.com/licensing/542.html.

\* cited by examiner

*Primary Examiner*—Sandra Saucier
*Assistant Examiner*—Satyendra K Singh
(74) *Attorney, Agent, or Firm*—Workman Nydegger

(57) ABSTRACT

A delivery system that includes a bone growth promoting material encapsulated within a water absorptive gelatinizable covering is used to promote bone growth in order to repair a bone defect and/or strengthen a weakened bone region. The delivery system may be shaped and sized in order to fit within a bleeding wound (e.g. one that is formed in the gingiva when a tooth is extracted). The covering may be formed of a gelatinizable gauze that forms a gel-like material when moistened with water. The delivery system is contained within a moisture resistant package prior to use. Alternatively, the delivery system comprises a bone growth promoting material and thickening agent contained within a syringe that, upon adding water, form a viscous gel or stiff putty.

18 Claims, 4 Drawing Sheets

DELIVERY SYSTEM FOR BONE GROWTH PROMOTING MATERIAL

BACKGROUND OF THE INVENTION

1. The Field of the Invention

The present invention relates to delivery systems and related compositions and methods for promoting and supporting bone growth.

2. The Relevant Technology

In dental work, it is often necessary to remove a tooth. Because the teeth are anchored to the jaw bone, removal of the tooth leaves a huge discontinuity or defect in the bone once occupied by the tooth root. In some cases, certain tooth extractions may require the removal of surrounding bone tissue. Whereas the body is, in theory, capable of growing new bone to fill in the discontinuity or defect, bone typically grows very slowly. In fact, bone grows much more slowly than soft tissue, which preferentially grows and fills in much of the void, leaving a weakened, defective bone that is more prone to fracture or failure, particularly in the elderly. Secondarily, once a tooth has been removed, the surrounding jaw bone can atrophy and weaken as a result of non-use in the area of the removed tooth.

In order to restore or augment areas where bone has been removed, naturally derived and synthetically manufactured bone mineral substitutes have been developed. These materials are often used to preserve or augment the alveolar portion of the jaw bone that supports the teeth, augment atrophic alveolar ridges (e.g. tooth socket bones which have decreased in size as a result of tooth removal), and to fill various periodontal defects. Under one current practice, bone mineral substitutes for promoting bone growth in the form of granules are manually delivered into the intended site using a spatula, spoon or other tool. In some cases, these granules are pre-mixed with blood to cause them to adhere together. This method often results in inadvertent spillage and placement of particles into unintended locations and in a general inability to form the material to fill the augmentation site as intended. This is especially the case when attempting to augment bone growth along a ridge, such as the alveolar ridge mentioned above.

In view of the foregoing, it would be an improvement in the art to provide improved delivery systems and related compositions and methods to overcome the aforementioned difficulties.

BRIEF SUMMARY OF THE PREFFERED EMBODIMENTS

The present invention relates to delivery systems and related compositions and methods that may be used to place materials that promote and support bone growth into a bone defect in order to preferentially promote bone growth over the growth of soft tissue. According to one embodiment, the delivery system includes a covering formed of a water-absorbing gelatinizable material, and a bone growth promoting material contained within the covering.

The covering may be formed of any water absorbing gelatinizable material. Suitable materials include, but are not limited to, gelatinizable gauze, oxidized cellulose, oxidized regenerated cellulose, cat gut, or any other hydrophilic absorbable polymer which may be woven, knitted, braided, or otherwise formed into a covering. The material of the covering may be resorbable or non-resorbable by the body, as desired.

Examples of bone growth promoting materials that may be used within the scope of the invention to promote and support the growth of bone into a defect include calcium hydroxyapatite, beta-tricalcium phosphate, purified coral shell, freeze dried natural bone powder, freeze dried natural bone particles, demineralized natural bone powder, and demineralized natural bone particles, shards or fragments. Such materials physically occupy the bone defect so as to (1) physically exclude or displace faster-growing soft tissue that might otherwise fill in an untreated void and (2) form a matrix into which bone can grow over time until the bone growth promoting material is absorbed into the bone and/or integrated into the new bone matrix.

The delivery system may be configured so as to have any desired size and shape. According to one embodiment, the delivery system can have an elongate sausage-like configuration. According to another embodiment, the delivery system can have a pillow-like configuration. The delivery systems according to the invention may be configured so as to fit within whatever size or shape bone effect is being treated.

In an alternative embodiment according to the invention, the bone growth promoting material is enclosed within a syringe, such as in the form of pellets, a powder or mixture of the two. According to one embodiment, the bone growth promoting material is mixed with a tissue adhesion agent, an example of which is the water-absorbing gelatinizable material discussed above, used to form a covering. A gelatinizable gauze or fiber can be chopped, cut-up, or ground into smaller pieces and mixed with the bone growth promoting material. Water or other appropriate solvent or vehicle is mixed with the bone growth promoting material and optional tissue adhesion agent in order to form a paste or gel that can be expressed onto a bone or into a bone defect by means of a syringe. In one embodiment, the water or other solvent or vehicle is added to the syringe and mixed with the bone growth promoting material just prior to use in order to prevent growth of bacteria. Alternatively, an anti-spoilage agent, such as benzalkonium chloride, methylparaben, ethylparaben, and the like, can be added to a pre-mixed composition suitable for long-term storage and subsequent delivery.

The present invention also includes related methods of delivering a bone growth promoting material into a bone defect. In the case of the delivery system comprising bone growth promoting material surrounded by a covering, the delivery device is placed into the bone defect using, e.g., tweezers or other suitable placement device. The covering, being formed of a water-absorbing gelatinizable material, advantageously forms a sticky material that is highly adhesive to bone or other tissue found within the bone defect. In this way, the delivery system is held in place in order to keep the bone growth promoting material within the bone defect. In an alternative method, a bone growth promoting material in the form of a paste or gel is expressed into a bone defect by means of a syringe, preferably in combination with a tissue adhesion agent that helps keep the bone growth promoting material in the desired location.

In order to further protect the bone growth promoting material from foreign debris and/or in order to help maintain the bone growth promoting material within the bone defect being repaired, it is within the scope of the invention to place a barrier layer over the bone growth promoting material. This may be accomplished, for example, by applying a polymerizable resin barrier layer by means of a syringe and then causing or allowing it to harder or cure (e.g., by light or chemical curing).

One preferred use of the inventive compositions, systems and methods is to preserve or restore the alveolar portion of the jaw bone which supports the teeth. When a tooth is removed, the underlying portion of the jaw bone contains a defect that can otherwise fill with soft tissue instead of bone. In addition, bone can atrophy and weaken as a result of non-use and removal of the tooth. Implanting a delivery system containing a bone growth promoting material fills in and strengthens the jaw bone by repairing the defect.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by references to specific embodiments thereof, which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

A detailed description of the delivery systems, compositions and methods of the invention will now be provided with specific reference to Figures illustrating preferred embodiments of the invention. It will be appreciated that like structures will be provided with like reference designations.

The delivery system for promoting bone growth according to one embodiment includes a covering formed of a water-absorbing gelatinizable material and a bone growth promoting and supporting material contained inside, or at least partially surrounding, the covering.

Figure 1A:
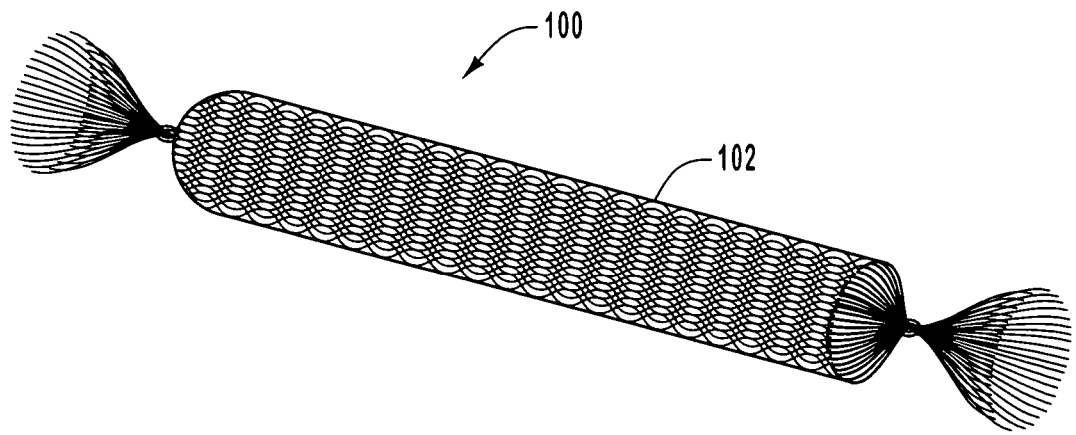
FIG. 1A is a perspective view of an embodiment of a delivery system according to the invention having a sausage-like configuration.

FIG. 1A is a perspective view illustrating one embodiment of a delivery system for promoting bone growth having a covering around at least a portion of a bone growth promoting material. Delivery system 100 includes a covering 102 that encapsulates a bone growth promoting material. In one embodiment, the covering 102 is formed of a water absorbing gelatinizable material, for example, gelatinizable gauze, oxidized cellulose, oxidized regenerated cellulose, cat gut, or any other hydrophilic absorbable polymer which may be woven, knitted, braided, or otherwise formed into a sheet, pouch, tube or other covering. The material of the covering may be resorbable or non-resorbable by the body, as desired.

In one embodiment, it advantageously becomes sticky and adhesive toward bone or other tissue where the delivery system 100 is placed.

The bone growth promoting material may be any material that can be used to promote and/or support the growth of bone tissue. Suitable materials may include at least one of calcium hydroxyapatite, beta-tricalcium phosphate, purified coral shell, freeze dried natural bone powder, freeze dried natural bone particles, demineralized natural bone powder, and demineralized natural bone particles, shards or fragments.

Figure 1B:
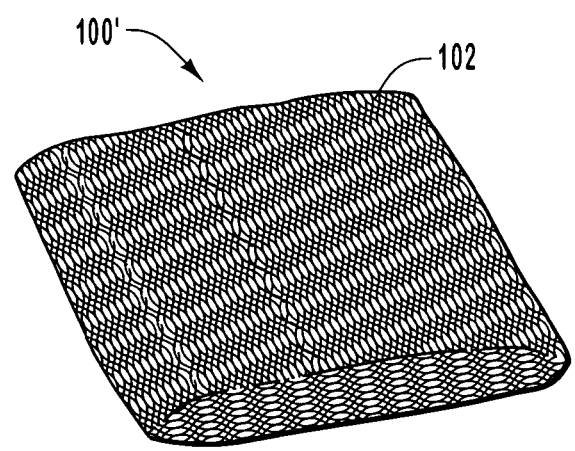
FIG. 1B is a perspective view of an embodiment of a delivery system according to the invention having a pillow-like configuration.

The covering 102 of the delivery system 100 may be woven, knitted or braided to be of any desired shape, size, length, or diameter. Methods of manufacturing the delivery system 100 will be explained in further detail below. According to the embodiment illustrated in FIG. 1A, the delivery system 100 may have an elongated sausage like configuration. FIG. 1B illustrates an alternative embodiment of a delivery system 100' having a pillow like configuration.

According to one embodiment, the delivery system 100 or 100' may also include an adhesive, for example, fibrin powder or chopped adhesive gauze, dispersed within the bone growth promoting material inside covering 102. Including an adhesive may be desirable when the delivery system 100 or 100' is used to promote and support bone growth along a ridge (e.g. an alveolar ridge). The adhesive helps to hold the material together so that the material is not easily displaced from the bone defect into unintended locations once, the covering 102 has sufficiently weakened.

The covering 102 as illustrated in FIGS. 1A-1B is formed of a water absorbing gelatinizable material. Suitable materials include gelatinizable thread, oxidized cellulose thread, and oxidized regenerated cellulose thread. These thread materials can be woven, knitted or braided into gauze, which can be used to form a covering 102 having a desired configuration. When the covering 102 is formed of oxidized cellulose thread or oxidized regenerated cellulose thread, the oxidation or oxidation/regeneration necessary to treat the cellulose thread may occur prior to or subsequent to weaving, knitting or braiding. In other words, the covering 102 may be woven, knitted or braided from cellulose thread when initially stronger, and then later chemically treated as desired.

Figure 2:
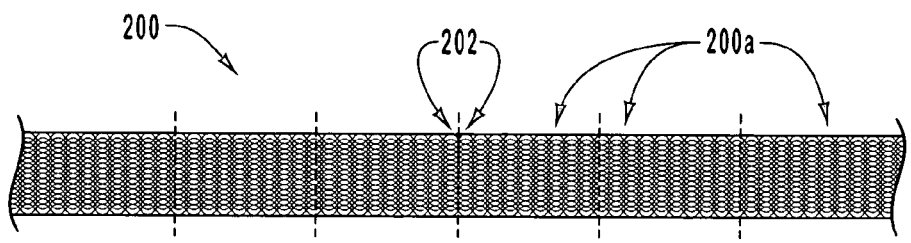
FIG. 2 is a perspective view of a hollow tube prior to sectioning to form individual delivery systems as illustrated in FIGS. 1A and 1B.

For example, the covering 102 of the delivery system 100 of FIG. 1A or delivery system 100' of FIG. 1B may be manufactured by forming a hollow tube 200, as illustrated in FIG. 2. The hollow tube 200 may be long enough to form a plurality of delivery systems 100 or 100'. Hollow tube 200 may be cut into several portions 200a, each portion to be made into a delivery system 100 or. The hollow tube portions 200a may then each be filled with bone growth promoting material, and the ends 202 of each tube portion 200a may then be sealed. The ends 202 may be sealed by tying with a thread, or the ends may be wet sealed. To wet seal the ends 202, each end 202 is closed, wetted with water, and then dried. The water is absorbed by the ends 202 of the covering, which gelatinizes and seals the end 202. Once dried, the result is a delivery system 100 as illustrated in FIG. 1A or delivery system 100' as illustrated in FIG. 1B.

The delivery system 100 or 100' is preferably stored within a moisture resistant package. Examples of such packaging include a foil pouch, a glass or plastic vial, a plastic container, or any other container formed of water resistant material.

The delivery system may be used to promote bone growth in a variety of circumstances. One preferred use is to preserve the alveolar portion of the jaw bone which supports the teeth. When a tooth is removed, the underlying portion of the jaw bone will contain a defect that can greatly weaken the bone. In addition, the bone may atrophy and weaken as a result of non-use and removal of the tooth. Implanting a delivery system containing a bone growth promoting material displaces soft tissue growth in favor of bone growth so as to strengthen the area of the jaw bone into which it is implanted.

Figure 3:
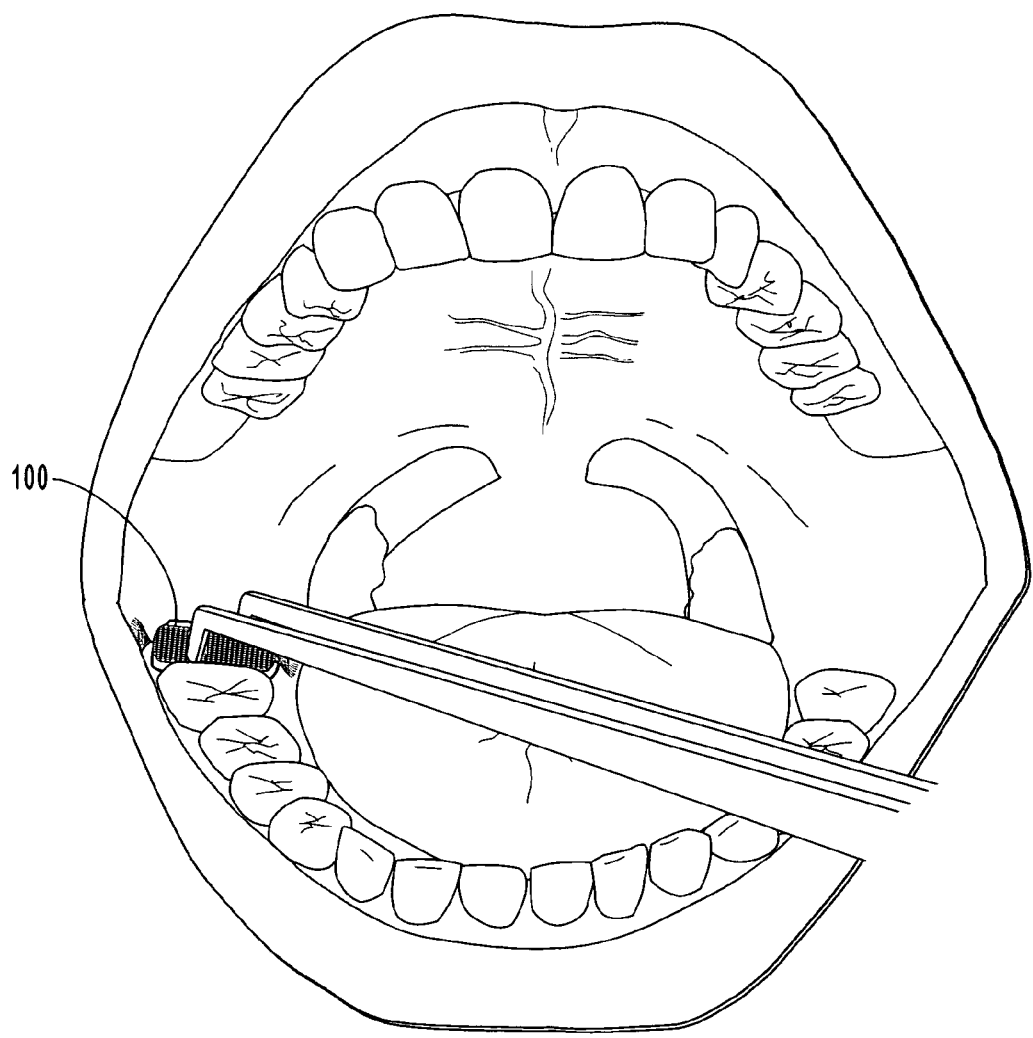
FIG. 3 is a perspective view of a tooth extraction site where a delivery system similar to the one illustrated in FIG. 1A is being placed.

FIG. 3 is a perspective view of a portion of a patient's mouth where the third molar has just been removed. A delivery system 100 is shown being placed into the void or defect left as a result of removal of the tooth from the jaw bone. The delivery system 100 is placed adjacent to the jaw bone tissue so as to selectively promote growth of the bone tissue and prevent the incursion of faster-growing soft tissue. As mentioned above, the covering 102 of the delivery system 100 may be resorbable or non-resorbable, as desired. It may also be adhesive in order to help maintain the delivery system 100 in place.

Either delivery system 100 or 100' can be used to promote bone growth along a ridge (e.g. alveolar ridge) or any other place where a bone defect or weakened bone exists. Other delivery systems of alternative shape and design could also be used as desired. When placed along a ridge, it may be desirable to include an adhesive dispersed within the material. The adhesive helps to hold and maintain the bone growth promoting material together so that it does not slide down the side of the ridge as the covering 102 weakens over time.

Figure 4A:
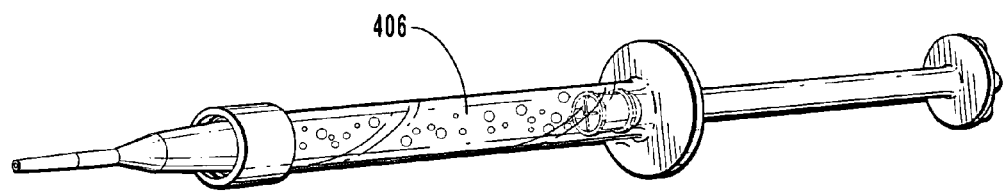
FIGS. 4A and 4B illustrate use of a syringe delivered bone growth promoting composition.
Figure 4B:
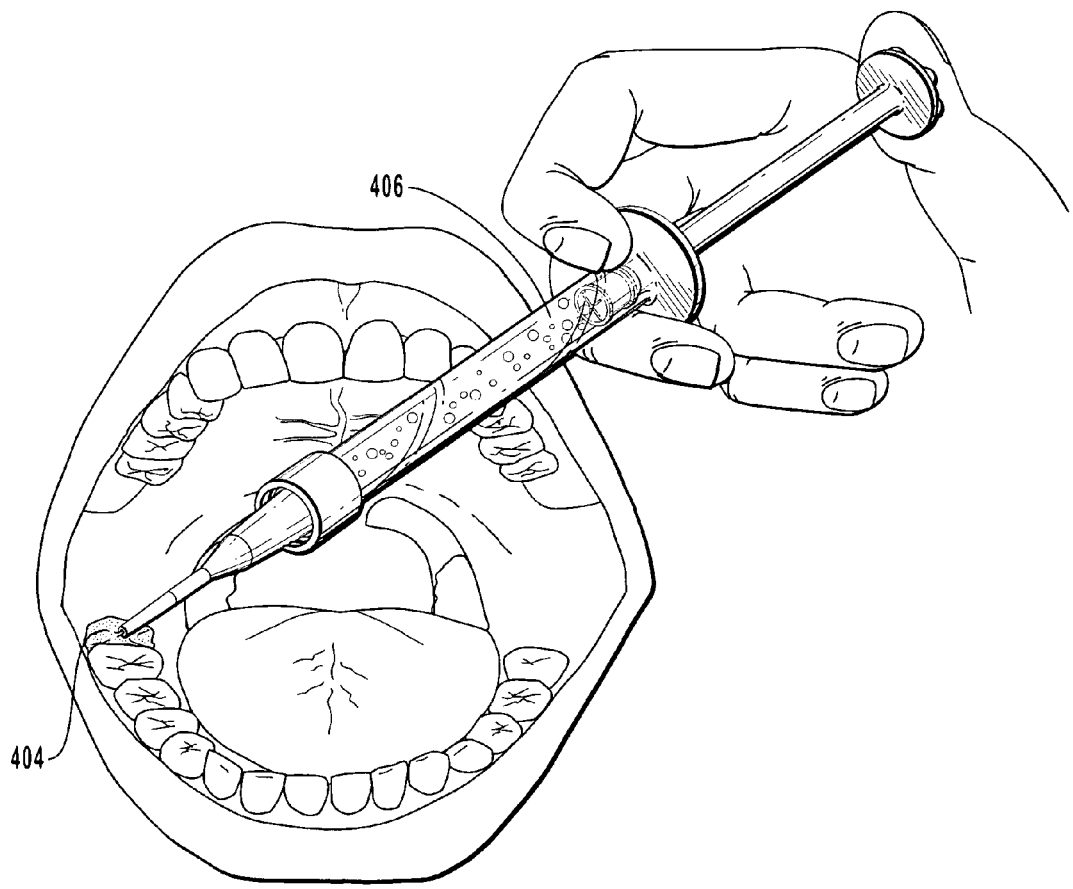

According to another embodiment within the scope of the invention, a syringe delivered bone growth promoting composition 404 may be dispensed from a syringe 406, as illustrated in FIGS. 4A and 4B. The composition 404 may comprise a bone growth promoting material in granule or powder form, and a thickener dispersed among the bone growth promoting material. The thickener may also be adhesive to tissue and may comprise any of gelatinizable gauze, oxidized cellulose, oxidized regenerated cellulose, or cat gut either ground up or in powder form. The thickener may alternatively comprise any proteinous material, for example, a biocompatible gelatinous collagen. The thickener is advantageously dispersed among the bone growth promoting material.

Upon the addition of water or other solvent or vehicle, the composition 404 is capable of forming a viscous gel or firm putty (depending on the amount of water added) that may be dispensed from the syringe 406. The composition 404 may initially be provided in either a dry or wet form. In other words, water may be added at the time of manufacture or later, by the dental practitioner. If provided in a wet form, a preservative (e.g., benzalkonium chloride, methylparaben, ethylparaben, and the like) capable of preventing growth of bacteria or other microorganisms is preferably included. The viscous gel or firm putty may be dispensed in the location desired, as illustrated in FIG. 4B, and in the case of a firm putty, may be formed as desired by the dental practitioner.

Figure 5:
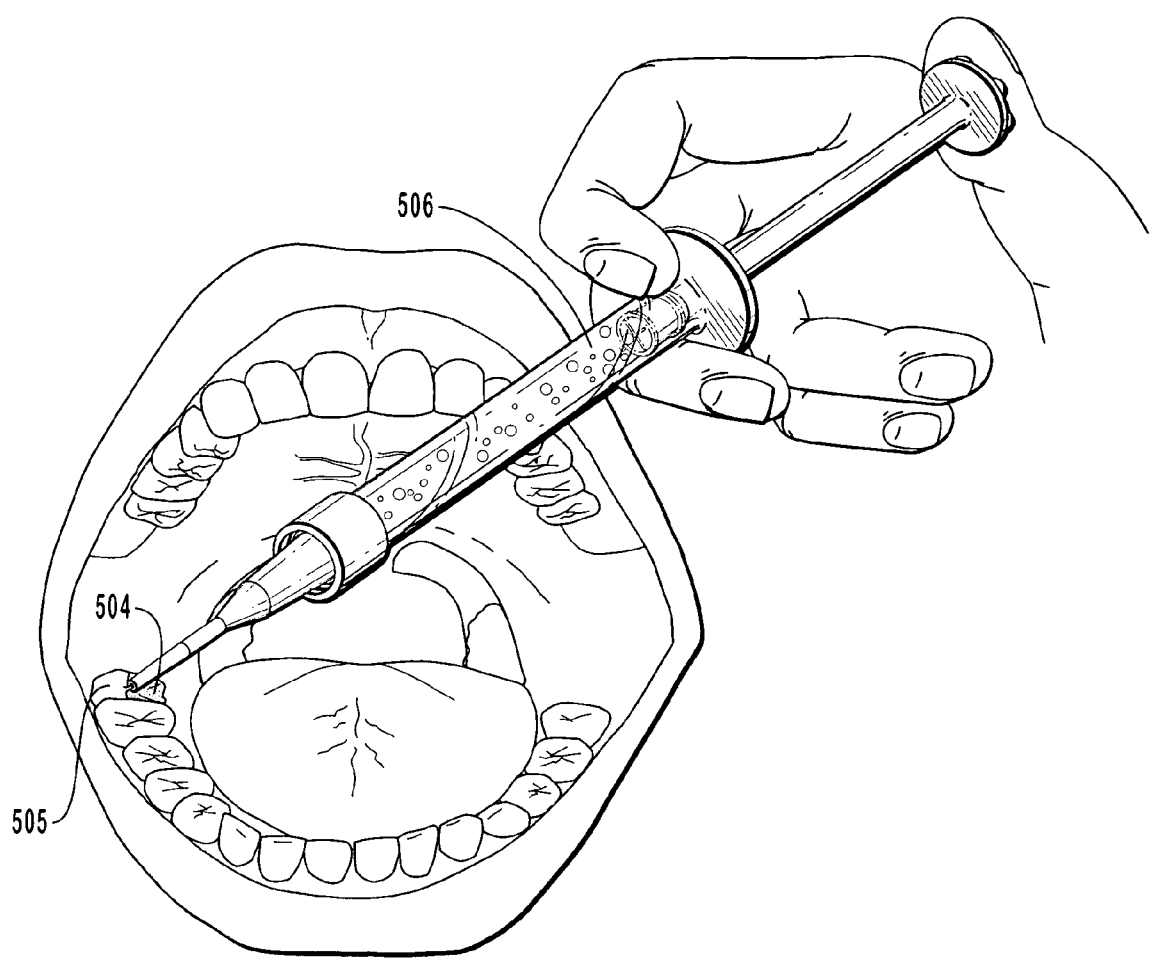
FIG. 5 illustrates an alternative method of augmenting bone growth with a bone growth promoting material and a syringe delivered polymerizable resin barrier layer.

FIG. 5 illustrates a further alternative embodiment. In this embodiment, a polymerizable resin 505 is delivered by a syringe 506 over bone growth promoting material 504 that has been packed adjacent to bone tissue to be augmented. The polymerizable resin preferably is a resorbable, biocompatible material that may be light or chemically cured. It acts as a barrier layer to prevent saliva or other fluids from carrying away the packed bone growth promoting material. It also reduces migration of fast-growing epithelial tissue down into the implanted material, thus facilitating bone growth in from the side. The bone is thereby allowed to grow into the packed bone growth promoting material free of completion from epithelial tissue.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A moisture activated implant device for placement into a tooth extraction site or other bone defect and promoting bone growth in the bone defect, comprising:
    a dry covering comprised of a water absorbing gelatinizable material that defines an enclosed space, wherein the dry covering consists essentially of oxidized cellulose; and
    a bone growth promoting material, disposed within the enclosed space defined by the dry covering, selected from the group consisting of hydroxyapatite, beta-tricalcium phosphate, purified coral shell, freeze dried natural bone powder, freeze dried natural bone particles, demineralized natural bone powder, demineralized natural bone particles, demineralized natural bone shards, demineralized natural bone fragments, and combinations thereof,
    wherein the dry covering encapsulates and retains the bone growth promoting material within the enclosed space prior to use and becomes gelatinous and adhesive upon contact with water so as to retain the bone growth promoting material within a tooth extraction site or other bone defect during use.

2. The implant device as recited in claim 1, wherein the implant device consists essentially of oxidized cellulose and the bone growth promoting material.

3. The implant device as recited in claim 1, wherein the water absorbing gelatinizable material is resorbable.

4. The implant device as recited in claim 1, wherein the implant device has an elongate sausage-like configuration.

5. The implant device as recited in claim 1, wherein the implant device has a pillow like configuration.

6. The implant device as recited in claim 1, further comprising moisture-resistant packaging within which the implant device is stored prior to use.

7. The implant device as recited in claim 1, wherein the implant device further comprises an adhesive dispersed with the bone growth promoting material for adhering the bone growth material together.

8. The implant device as recited in claim 7, wherein the adhesive comprises at least one of fibrin powder or chopped adhesive gauze.

9. A method of manufacturing the implant device for promoting bone growth according to claim 1, comprising:
    forming the water absorbing gelatinizable material into a hollow tube or pouch;
    inserting the bone growth promoting material into at least a portion of the tube or pouch; and
    closing the open ends of the tube or pouch filled with the bone growth promoting material to form the implant device for promoting bone growth.

10. The method of manufacturing as recited in claim 9, wherein the act of closing the open ends of the tube or pouch comprises wet sealing and then drying the ends.

11. The method of manufacturing as recited in claim 9, wherein the tube or pouch is divided into a plurality of individual sections that are separated and individually sealed so as to form a plurality of implant devices from a single tube or pouch filled with the bone growth promoting material.

12. A method of promoting bone growth within a tooth extraction site or other bone defect, comprising:

providing the implant device recited in claim 1, the covering of the implant device being dry and initially nonadhesive; and placing the implant device within a tooth extraction site or other bone defect; wherein the covering of the implant device becomes gelatinous and adhesive upon contact with water and retains the bone growth material within the tooth extraction site or other bone defect.

13. The method as defined in claim 12, wherein the implant device is placed into a bone defect resulting from the removal of a tooth.

14. A moisture activated implant device for placement into a tooth extraction site or other bone defect and promoting bone growth in the bone defect, comprising:

a dry covering comprised of a water absorbing gelatinizable material that defines an enclosed space, wherein the dry covering consists essentially of oxidized cellulose;

a bone growth promoting material in granule or powder form disposed within the enclosed space defined by the dry covering, wherein the bone growth promoting material comprises hydroxyapatite, beta-tricalcium phosphate, purified coral shell, natural bone, demineralized natural bone, or a combination thereof; and a thickener dispersed among the bone growth promoting material, the thickener comprising a material that forms a viscous gel or firm putty upon contact with water, wherein the dry covering encapsulates and retains the bone growth promoting material within the enclosed space prior to use and becomes gelatinous and adhesive upon contact with water so as to retain the bone growth promoting material within a tooth extraction site or other bone defect during use.

15. The implant device as recited in claim 14, wherein the implant device consists essentially of oxidized cellulose, the bone growth promoting material, and the thickener.

16. The implant device as recited in claim 14, wherein the thickener comprises at least one of gelatinizable gauze, oxidized cellulose, oxidized regenerated cellulose, ground catgut, or powdered catgut.

17. The implant device as recited in claim 14, wherein the thickener comprises a biocompatible gelatinous collagen material.

18. The implant device as in recited in claim 14, wherein the dry covering is woven, knitted, or braided.

* * * * *

UNITED STATES PATENT AND TRADEMARK OFFICE
CERTIFICATE OF CORRECTION

PATENT NO. : 7,534,264 B2
APPLICATION NO. : 10/766503
DATED : May 19, 2009
INVENTOR(S) : Dan E. Fischer It is certified that error appears in the above-identified patent and that said Letters Patent is hereby corrected as shown below:

<u>Column 2</u>
Line 20, change "bone effect is being" to --of bone defect being--

<u>Column 4</u>
Line 27, change "once, the" to --once the--
Line 48, change "100 or." to --100 or 100' "--

<u>Column 8</u>
Line 20, change "as in recited" to --as recited--

Signed and Sealed this

Twenty-first Day of July, 2009

JOHN DOLL
*Acting Director of the United States Patent and Trademark Office*